United States Patent
Higashi et al.

(10) Patent No.: US 6,951,966 B1
(45) Date of Patent: Oct. 4, 2005

(54) ORTHOALKYLATION CATALYST FOR PHENOL AND PROCESS FOR PRODUCING ORTHOALKYLATED PHENOL WITH USE THEREOF

(75) Inventors: Mitsuhiro Higashi, Wakayama (JP); Masamitsu Tanaka, Wakayama (JP); Kenji Ekawa, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 09/555,255

(22) PCT Filed: Sep. 28, 1999

(86) PCT No.: PCT/JP99/05273

§ 371 (c)(1),
(2), (4) Date: Jul. 26, 2002

(30) Foreign Application Priority Data

Sep. 28, 1998 (JP) .......................................... 10-273160

(51) Int. Cl.$^7$ .............................................. C07C 37/00
(52) U.S. Cl. ........................ 568/804; 502/324; 502/340
(58) Field of Search .......................... 568/804; 502/324, 502/340

(56) References Cited

U.S. PATENT DOCUMENTS

| | | | |
|---|---|---|---|
| 3,968,172 A | * 7/1976 | Ichikawa et al. | 568/804 |
| 4,528,407 A | * 7/1985 | Smith et al. | 568/804 |
| 4,554,266 A | * 11/1985 | Bennett et al. | 502/340 |
| 4,851,591 A | * 7/1989 | Battista et al. | 568/804 |
| 4,900,708 A | * 2/1990 | Bennett et al. | 502/340 |
| 4,933,509 A | * 6/1990 | Warner | 568/804 |
| 5,847,237 A | * 12/1998 | Yago et al. | 568/804 |

FOREIGN PATENT DOCUMENTS

| | | |
|---|---|---|
| JP | 426894 | 3/1942 |
| JP | 4621371 | 6/1971 |

OTHER PUBLICATIONS

Patent Abstracts of Japan: Publication No. 07265710; Date of Publication Oct. 17, 1995; Title—Orthoalkylation Catalyst of Phenols, Precursor Thereof and Production of Orthoalkylated Phenols Using Catalyst; Inventor—Yago Shunji et al., Applicant—Honshu Chem Ind Co Ltd.

Abstract: Patent No. JP59228940; US Equivalent—4,554,267; Publication Date of U.S. Patent Nov. 19, 1985; Title—Catalyst and Method for Ortho–Alkylation of Hydroxyaromatic Compounds; Inventor—Gregory R. Chambers et al.; Applicant—Gen Electric.

* cited by examiner

*Primary Examiner*—Michael L. Shippen
(74) *Attorney, Agent, or Firm*—Birch, Stewart, Kolasch & Birch, LLP

(57) ABSTRACT

The orthoalkylation catalyst for phenols of the invention is one produced by calcining a catalyst precursor comprising basic magnesium carbonate (a) and magnesium oxide (b) optionally together with manganese oxalate (c), the basic magnesium carbonate (a) and magnesium oxide (b) being mixed together at a weight ratio ((a)/(b)) of 20/80 to 80/20. The process for producing an orthoalkylated phenol according to the invention comprises performing a vapor phase reaction of a phenol with an alkyl alcohol in the presence of the above orthoalkylation catalyst so that an orthoalkylated phenol is obtained.

The invention enables obtaining an orthoalkylation catalyst for phenols which has high activity and high selectivity, has long catalytic life and exhibits more stable catalytic life than those of conventional orthoalkylation catalysts for phenols. Moreover, by virtue of the use of the catalyst capable of exerting these effects, there can be obtained a process for producing an orthoalkylated phenol which ensures prolonged and constant catalyst regeneration cycle.

11 Claims, No Drawings

US 6,951,966 B1

ORTHOALKYLATION CATALYST FOR PHENOL AND PROCESS FOR PRODUCING ORTHOALKYLATED PHENOL WITH USE THEREOF

This application is the national phase under 35 U.S.C. § 371 of PCT International Application No. PCT/JP99/05273 which has an International filing date of Sep. 28, 1999, which designated the United States of America.

TECHNICAL FIELD

The present invention relates to a catalyst for alkylating the ortho position of phenols (herein referred to as "orthoalkylation catalyst") and to a process for producing an orthoalkylated phenol with the use of the catalyst. More particularly, the present invention relates to an orthoalkylation catalyst for phenols, which enables alkylating a phenol having a hydrogen atom of at least one ortho position thereof with an alkyl alcohol to thereby obtain an orthoalkylated phenol, and relates to a process for producing an orthoalkylated phenol with the use of the catalyst.

BACKGROUND ART

Examples of orthoalkylated phenols used in industrial fields include 2, 6-xylenol as a raw material for producing polyphenylene oxide resins, 2,3,6-trimethylphenol as a starting material for synthesizing vitamin E,.and o-cresol, 2,5-xylenol, 2,3-xylenol, 2,4-xylenol, 2,4,6-trimethylphenol, methylhydroquinone or the like as a starting material or an intermediate of medicine, agricultural chemicals, resins, various additives, industrial chemicals, etc.

Methods of orthoalkylating a phenol having a hydrogen atom of at least one ortho position thereof with an alkyl alcohol in the presence of an alkylation catalyst are known in the art. In these methods, a phenol is reacted with an alkyl alcohol in a vapor phase in the presence of a catalyst composed only of magnesium oxide, a catalyst composed of magnesium oxide coated with copper, or a catalyst composed of magnesium oxide and a co-catalyst of manganese salt as bases.

The catalyst composed only of magnesium oxide is, for example, the magnesium oxide catalyst described in Japanese Patent Publication No. 42(1967)-6894, which is prepared by compression molding powder of basic magnesium carbonate and calcining the molding.

The catalyst composed of magnesium oxide coated with copper is, for example, the catalyst composition described in Japanese Patent Laid-open Publication No. 59(1984)-228940, which comprises magnesium oxide containing copper about 0.1% by weight based on magnesium oxide, wherein this copper is adhered on magnesium oxide either, the copper being either in elemental form being a shape of a layer of submicroscopic thickness or in chemically bonded form. This catalyst composition is prepared by first preparing at about 50 to 100° C. a slurry, in an aqueous solution, of at least one copper salt of a substantially water insoluble magnesium reagent capable of forming magnesium oxide upon calcination (at least one member of magnesium oxide, magnesium hydroxide and magnesium carbonate), subsequently controlling the copper content of the slurry to thereby obtain a magnesium-containing solid layer having a copper coating of submicroscopic thickness, and thereafter drying the solid layer and effecting calcination thereof.

The catalyst composed of magnesium oxide and a co-catalyst of manganese salt as bases is, for example, the catalyst composed of magnesium oxide and manganese sulfate described in Japanese Patent Publication No. 46(1971)-21371. This catalyst is prepared either by pulverizing magnesium oxide and mixing the resultant powder with manganese sulfate or by impregnating magnesium oxide with manganese sulfate and subjecting the impregnated magnesium oxide to drying, molding and calcining.

These conventional orthoalkylation catalysts for phenols containing magnesium oxide are industrially employed, for example, in the production of 2,6-xylenol from phenol as a starting material. They, although thus meeting the objective to a certain extent, suffer from the degradation as-inherently exhibited by magnesium oxide containing catalysts. Therefore, further enhancement of the catalytic performance thereof is demanded from the industrial point of view.

In Japanese Patent Laid-open Publication No. 7(1995)-265710, the same applicant disclosed, as a catalyst of high selectivity that exhibits catalytic performance improved over the conventional magnesium oxide containing catalysts, an orthoalkylation catalyst for phenols produced by calcining a catalyst precursor composed of a dry mixture of manganese oxalate (a), fine particles of a phenol resin (b) and at least one magnesium compound selected from among basic magnesium carbonate and magnesium oxide.

However, there is a demand for the development of an orthoalkylation catalyst for phenols which is superior to this catalyst in respect of activity, selectivity, catalytic life and stability, and further the development of a process for producing an orthoalkylated phenol with the use of the above orthoalkylation catalyst.

Therefore, the objective of the present invention is to provide an orthoalkylation catalyst for phenols which exhibits high activity and high selectivity, has prolonged catalytic life and is stable, and to provide a process for producing an orthoalkylated phenol with the use of the orthoalkylation catalyst.

DISCLOSURE OF THE INVENTION

The orthoalkylation catalyst for phenols according to the present invention is characterized in that it is produced by calcining a catalyst precursor comprising basic magnesium carbonate (a) and magnesium oxide (b), the basic magnesium carbonate (a) and magnesium oxide (b) being mixed together at a weight ratio ((a)/(b)) of 20/80 to 80/20.

Further, the process for producing an orthoalkylated phenol according to the present invention is characterized in that it comprises performing a vapor phase reaction of a phenol with an alkyl alcohol in the presence of the above orthoalkylation catalyst for phenols of the present invention so that an orthoalkylated phenol is obtained.

BEST MODE FOR CARRYING OUT THE INVENTION

The orthoalkylation catalyst for phenols of the present invention and the process for producing an orthoalkylated phenol with the use of the orthoalkylation catalyst will be described below.

Orthoalkylation Catalyst

The orthoalkylation catalyst for phenols of the present invention will first be described.

The orthoalkylation catalyst for phenols of the invention is one produced by calcining a catalyst precursor comprising basic magnesium carbonate (a) and magnesium oxide (b) optionally together with manganese oxalate (c)

Basic Magnesium Carbonate (a)

It is generally preferred that the basic magnesium carbonate (a) for use in the present invention be in the form of industrially obtained fine powder. Although both light and ground commercially available products can be also utilized, the use of heavy magnesium carbonate is preferred.

In the preparation of the catalyst precursor of the present invention, the basic magnesium carbonate (a) is used in such an amount that the basic magnesium carbonate (a) and magnesium oxide (b) are mixed together at a weight ratio ((a)/(b)) of 20/80 to 80/20, preferably20/80 to 70/30, and still preferably 30/70 to 60/40.

Magnesium Oxide (b)

In the present invention, the magnesium oxide (b) is used as a binder (binding agent) component during the preparation of the catalyst precursor and functions as a catalyst component after the calcination. For example, light burned magnesia is used. Especially, varieties of low activity, for example, 10 to 100 in terms of iodine value are preferred from the viewpoint of the moldability of catalyst precursor.

In the preparation of the catalyst precursor of the present invention, the magnesium oxide (b) is used in such an amount that the basic magnesium carbonate (a) and magnesium oxide (b) are mixed together at a weight ratio ((a)/(b)) of 20/80 to 80/20, preferably 20/80 to 70/30, and still preferably 30/70 to 60/40. When the magnesium oxide (b) is used in this mixing weight ratio, the scatter of binding strength between catalyst particles is extremely slight in the catalyst molding (catalyst pellet) prepared by forming the catalyst precursor into, for example, pellets and calcining the formed catalyst precursor, so that a catalyst having prolonged catalytic life and being stable can be obtained. Conventional orthoalkylation catalysts of magnesium oxides exhibiting high activity at low temperatures are highly exothermic during the molding of catalyst precursor, so that the pelletization thereof is difficult. Furthermore, the conventional orthoalkylation catalysts of magnesium oxides have a drawback in that the binding strength between catalyst particles in the catalyst pellets is likely to lower, so that, during the use thereof, the catalyst molding is collapsed to thereby become powder with the result that the void ratio is decreased and the catalytic function is lost. On the other hand, orthoalkylation catalysts in which the binding strength between catalyst particles is satisfactory and its lowering is hardly perceived have a drawback in that the activity is so low that the cycle of catalyst regeneration, catalyst replacement, etc. is shortened with the result that the operation period of production apparatus is unfavorably reduced. The orthoalkylation catalyst for phenols of the present invention has resolved these mutually contradictory problems by mixing the basic magnesium carbonate (a) with the magnesium oxide (b) at the above ratio in the preparation of the catalyst precursor.

Manganese Oxalate

The manganese oxalate (c) optionally added in the present invention is a co-catalyst. From the viewpoint of homogeneous mixability, fine particles of manganese oxalate are preferred. Both a hydrate and a nonhydrate thereof may be preferably used.

The manganese oxalate (c) is optionally used in an amount of at least 0.1% by weight, preferably 0.1 to 10% by weight, based on the total (100% by weight) of basic magnesium carbonate (a) and magnesium oxide .(b) in the preparation of the catalyst precursor of the invention.

Preparation of Catalyst

The orthoalkylation catalyst for phenols of the present invention is prepared, for example, by first conducting dry mixing of given amounts of basic magnesium carbonate (a) and magnesium oxide (b) optionally together with manganese oxalate (c) with the use of a blender or other mechanical mixing device to thereby homogeneously disperse them (catalyst precursor), subsequently adding water and milling the mixture, next forming the milled mixture into a molding such as pellets by extrusion or other means and thereafter calcining the obtained molding (e.g., pellets of catalyst precursor) to thereby attain activation thereof.

In the above preparation of the catalyst precursor, conventional common molding auxiliaries such as graphite and magnesium stearate can be optionally added to the basic magnesium carbonate (a), magnesium oxide (b) and manganese oxalate (c) in an amount not detrimental to the objective of the invention. These molding auxiliaries are used according to necessity in an amount of generally 0.1 to 5% by weight based on the total (100% by weight) of basic magnesium carbonate (a) and magnesium oxide (b).

The calcination is satisfactorily accomplished by heating the above molding of catalyst precursor at 300° C. or higher, generally 300 to 500° C., and preferably 350 to 500° C., for obtaining an active catalyst. In the present invention, it is especially preferred that the molding of catalyst precursor be heated at the above temperature in the absence of molecular oxygen. The activation of the catalyst precursor under these conditions is generally satisfactorily accomplished by the calcination not exceeding 24 hr.

In the invention, the above calcination is preferably performed in an atmosphere in which molecular oxygen is not present, generally in an inert gas, such as a nitrogen stream. Further, the vapors of raw materials for use in the orthoalkylation reaction of phenols, i.e. phenol, alkyl alcohol or mixture thereof, can be flowed through the calcination atmosphere. When molecular oxygen is present in the calcination atmosphere during the activation of the catalyst precursor by the calcination, combustion reaction occurs not to thereby obtain satisfactory catalytic performance and cause the resultant catalyst to have not only lowered catalytic activity but also lowered mechanical strength with the result that the catalyst life is shortened.

In the invention, the activation of the catalyst precursor by the calcination can be effected prior to the charging of the molding of the catalyst precursor into a reactor or alternatively after the charging of the molding of the catalyst precursor into a reactor, that is, in the reactor. Generally, first charging the molding of the catalyst precursor into a reactor and thereafter effecting the calcination for activation is industrially advantageous. For example, the activation can be accomplished by first charging the molding of the catalyst precursor into a reactor and thereafter contacting the same with the nitrogen or vapor of fed raw material mixture having been preheated to desirable temperature as required for the activation of the catalyst precursor to thereby calcine the catalyst precursor.

The above calcination of the catalyst precursor induces, for example, decarbonation of the manganese oxalate (c) and dehydration and decarbonation of the basic magnesium carbonate (a) so that not only is the catalyst precursor activated but also pores are formed in the resultant catalyst to thereby enable obtaining an increased catalytic surface area. It is generally preferred that the catalyst have a surface area of at least 25 $m^2/g$, especially 25 to 500 $m^2/g$. Generally, this surface area can be easily obtained by carrying out the calcination under the above conditions in accordance with the present invention.

The thus obtained orthoalkylation catalyst contains manganese in an amount of at least 0.1% by weight, preferably 0.2 to 5% by weight, based on the weight (100% by weight) of the catalyst.

Process for Producing Orthoalkylated Phenol

The process for producing an orthoalkylated phenol with the use of the catalyst obtained in the above manner will now be described.

The above orthoalkylation catalyst for phenols of the invention effectively acts for the accomplishment and continuation of alkyl substitution on the aromatic ring in the orthoalkylation of phenols.

The process for producing an orthoalkylated phenol according to the invention comprises performing a vapor phase reaction of a phenol with an alkyl alcohol in the presence of the orthoalkylation catalyst for phenols of the invention so that an orthoalkylated phenol is obtained.

The phenol for use in the invention can be, for example, a compound represented by the following formula [I]:

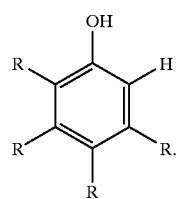

(I)

In the above formula [I], each of Rs independently represents a hydrogen atom, an alkyl group having 1 to 12 carbon atoms, phenyl group, an alkyl substituted phenyl group or hydroxyl group.

The alkyl group of the above alkyl substituted phenyl group generally has 1 to 12 carbon atoms.

Preferred Rs each independently represent a hydrogen atom, methyl group, hydroxyl group or a methyl substituted phenyl group.

Therefore, preferred examples of these phenols include phenol, o-cresol, m-cresol, 2,3-xylenol, 2,5-xylenol, 3,4-xylenol, 3,5-xylenol, hydroquinone and resorcinol. In the present invention, these phenols can be used either individually or in combination according to the necessity.

The alkyl alcohols for use as an alkylating agent in the invention are alkyl alcohols having 1 to 16 carbon atoms, preferably 1 to 12 carbon atoms, and especially preferably 1 to 6 carbon atoms, which may be saturated alcohols having a branched chain form, a linear chain form or alicyclic form. Examples of the alkyl alcohols include methyl alcohol, ethyl alcohol, n-propyl alcohol, isopropyl alcohol, n-butyl alcohol, isobutyl alcohol, amyl alcohol, isoamyl alcohol, hexyl alcohol, heptyl alcohol, octyl alcohol, nonyl alcohol, decyl alcohol, lauryl alcohol, cetyl alcohol, cyclohexyl alcohol and cyclohexylmethyl alcohol. Of these, methyl alcohol is most especially preferred. That is, the process of the invention is the most suitable to the production of orthomethylated phenols.

These alkyl alcohols are generally fed in excess in carrying out the reaction. Thus, after the reaction, the alkyl alcohols are recovered and recycled. Ethers corresponding to the alcohols are simultaneously recovered as by-products, which can also be effectively used as the alkylating agent.

The process for producing an orthoalkylated phenol according to the invention will be described in more detail below. The raw material mixture containing phenols and alkyl alcohols is vaporized by a preheater and introduced into a reactor. The inside of the reactor has been charged with the aforementioned activated orthoalkylation catalyst of the invention. The temperature of the system is controlled by heating so that the temperature within the reactor is maintained at 350 to 600° C., preferably 350 to 550° C., and still preferably 430 to 550° C.

With respect to the reaction temperature in the invention, relatively low temperatures are preferred for mainly producing mono-o-alkyl-substituted phenols, and high temperatures are preferred for mainly producing 2,6-dialkyl-substituted phenols. However, raising the reaction temperature to 550° C. or higher is unfavorable because it accelerates the thermal decomposition of alkyl alcohols employed to thereby bring unnecessary loss of alkyl alcohols.

For maximizing the yield of desired orthoalkylated phenols, at least one mole, preferably 1 to 3 moles., of an alkyl alcohol is used per ortho position of the aromatic ring of phenols to be alkylated. For example, when 2,3,6-trimethylphenol is produced by methylating m-cresol having two ortho hydrogen atoms per molecule, 2 to 6 moles of methyl alcohol is preferably used per mole of m-cresol. When the amount of alkyl alcohol per ortho position of the aromatic ring of other phenols to be alkylated exceeds 3 moles, the amount of undesired higher alkylation products is unfavorably simultaneously increased although the yield of desired mono- or dialkyl-substituted phenols is enhanced.

In the industrial process for producing an orthoalkylated phenol according to the invention, the molar ratio of alkyl alcohol/phenol is decided on so as not only to minimize the amount of unreacted raw materials to be recovered and recycled but also to maximize the selectivity for desired orthoalkylated final product (namely, substituted phenol having an alkyl substituent at one ortho position (2-position) or each of two ortho positions (2-and 6-positions) of the aromatic ring of the phenols).

Moreover, in the invention, when the raw material mixture containing phenols and alkyl alcohols is vaporized by a preheater and introduced into a reactor, it is preferred that water be simultaneously introduced together with the raw material mixture into the reactor. The amount of the water is generally at least 0.5 mole, preferably 1 to 4 moles, per mole of phenol. The water introduction is advantageous in that the catalyst activity can be maintained for a prolonged period, which is especially advantageous from the industrial view point.

In the invention, in the vapor phase reaction the duration of contact between the vapor of raw material mixture containing phenols and alkyl alcohols, and the catalyst is generally in the range of 0.01 to 10 hr$^{-1}$ in terms of liquid space velocity (LHSV) based on the raw material phenols. The "liquid space velocity" used herein is defined as the liquid volume of raw material phenol fed per hour and per catalyst unit as commonly meant with respect to the vapor phase reaction. In industry, the liquid space velocity is appropriately changed in conformity with the reaction conditions, and controlled at the optimum liquid space velocity by taking the relationship between production speed and catalyst life.

In the invention, although the above reaction is generally performed under atmospheric pressure, the reaction can be effected under any desired pressure which may be superatmospheric or subatmospheric. The reaction vapor led outside the reactor is cooled and condensed, and subjected to oil/water separation and, thereafter, the reaction mixture is separated into each component and purified with customary unit operations such as crystallization and distillation.

EFFECT OF THE INVENTION

The present invention enables obtaining an orthoalkylation catalyst for phenols which exhibits high activity and high selectivity and has prolonged catalytic life, which catalytic life is more stable than those of conventional orthoalkylation catalysts for phenols.

Furthermore, by virtue of the use of the catalyst capable of exerting the above effects, the present invention enables obtaining a process for producing an orthoalkylated phenol in which the period until regeneration of the catalyst is required is prolonged and stable.

EXAMPLE

The present invention will be further described with reference to the following Examples, which in no way limit the scope of the invention.

Example 1

Preparation of Catalyst Precursor Molding 140 g of heavy basic magnesium carbonate, 60 g of light burned magnesia (trade name: Kyowamag 20, produced by Kyowa Chemical Industry Co., Ltd.) and 4.9 g of manganese oxalate were charged into a beaker of 1 lit. capacity, and satisfactorily mixed and agitated.

Subsequently, 150 g of ion-exchanged water was added to 200 g of the above obtained raw material mixture, and milling and mixing thereof was carried out. Thus, a homogeneous bulk mixture was obtained.

The bulk mixture was charged into an extruder equipped with 3 mm $\phi$ dice and extruded into noodles of 3 mm diameter.

These noodles were placed in a 100° C. thermostatic chamber to thereby dry them, cut into 5 to 10 mm by a crushing sizer and passed through a 7-mesh sieve. Thus, a catalyst precursor molding of 3 mm diameter was obtained.

The bulk density of the obtained catalyst precursor molding was 0.64 g/ml, and the crushing strength (transverse direction), measured by Kiya type digital hardness tester (trade name: KHT-20, Fujiwara Scientific Co., Ltd.), was 4.6 kg.

Preparation of Catalyst by Calcination of Catalyst Precursor and Orthomethylation of Phenol 2,3,6-trimethylphenol was produced by orthomethylating m-cresol in the presence of the above prepared catalyst precursor with the use of the following experimental reactor, and the catalytic performance was evaluated.

The experimental reactor is composed of a reaction tube equipped with a preheater and vaporization layer for a raw material mixture containing a phenol and an alkyl alcohol; and a receiver equipped with a water cooling pipe for condensing and collecting a reaction product. The bottom of the reaction tube is connected via a stainless steel conduit to the water cooling pipe.

This reaction tube is made of a stainless steel pipe of ½ inch diameter and 40 cm length, and arranged so as to extend in the vertical direction.

25 ml of the above catalyst precursor was charged into the reaction tube, and heated to 370° C. while causing nitrogen gas to flow through the catalyst layer at a rate of 6000 ml/hr. The temperature was maintained for 15 min, and thereafter a mixture of m-cresol, methyl alcohol and water (molar ratio 1/4/3) was introduced in the catalyst layer. The feeding speed of the mixture was 30.2 g/hr, which was 1.2 g/cc/hr in terms of liquid space velocity. In that instance, the liquid space velocity (LHSV) based on m-cresol was 0.45 g/cc/hr. The LHSV based on m-cresol is an index that is convenient from the industrial point of view. Therefore, this index will be employed in the following Examples.

Orthomethylating reaction of m-cresol was performed under atmospheric pressure. The reaction temperature was regulated so that the concentration of desired product 2,3,6-trimethylphenol in the oil layer was maintained at 65±1%. The thus obtained reaction product was allowed to stand still, and the water layer was separated off. Part of the remaining oil layer was fractionated and analyzed by gas chromatography. The analysis was conducted periodically (every two hours) to thereby monitor the concentration of 2,3,6-trimethylphenol. When the concentration of 2,3,6-trimethylphenol became below 65±1%, the operation of raising the reaction temperature by 1 to 2° C. was effected.

The reaction was continued until reaching 500° C. while raising the reaction temperature in conformity with the degradation of the catalyst. The reaction time until reaching 500° C. was measured as an index of the catalyst life (hereinafter, this reaction time referred to as "catalyst life"). The composition of the product was expressed by the average in terms of % by weight over the entire reaction time.

The catalyst having been activated by calcining the catalyst precursor molding, at the initial stage, exhibits the highest catalytic activity so that the reaction temperature can be set low. Thus, the reaction temperature at the initial stage of the reaction in which the desired product 2,3,6-trimethylphenol can be obtained in the oil layer at a concentration of 65±1% is given below as "initial temperature of reaction".

The reaction results are specified in Table 1.

TABLE 1

| | Initial temp. of reaction | Av. product compsn. [wt. %] | | | | Catalyst life [hr] |
|---|---|---|---|---|---|---|
| | [° C.] | C | 25X | 236T | 2346T | |
| Example 1 | 468 | 2.8 | 20.5 | 65.0 | 1.6 | 596 |

(Note)
C: m-cresol,
25X: 2,5-xylenol,
236T: 2,3,6-trimethylphenol,
2346T: 2,3,4,6-tetramethylphenol.

Regeneration of Catalyst

When the concentration of 2,3,6-trimethylphenol in the reaction mixture became lower than 65±1% at the reaction temperature of 500° C., in the nitrogen atmosphere, the feeding of the raw material mixture and the external heating were terminated and the temperature of the catalyst layer was lowered. Upon arrival of the temperature of the catalyst layer at 350° C., the feeding of nitrogen gas was terminated and air was introduced in the catalyst layer. While inspecting the exothermic condition, decoking was gradually promoted. Decoking was continued until the reaction temperature of the catalyst layer finally became 450° C. After confirming that there was no longer any heat generation, the introduction of air was terminated and nitrogen gas was fed into the catalyst layer. In the same manner as above, the raw material mixture containing phenol and alkyl alcohol was fed to the preheater and vaporized, thereby carrying out the orthoalkylating reaction of m-cresol in the catalyst layer.

The crushing strength (transverse direction), measured by Kiya type digital hardness tester, of the thus regenerated catalyst was 0.8 kg. The results are given in Table 5.

Example 2

Catalyst precursor molding of 3 mm diameter was prepared from 140 g of heavy basic magnesium carbonate, 140 g of light burned magnesia (trade name: Kyowamag 20, produced by Kyowa Chemical Industry Co., Ltd.) and 4.9 g of manganese oxalate in the same manner as in Example 1. The obtained catalyst precursor molding was charged into the reactor and activated in the same manner as in Example 1, and the catalytic performance thereof was evaluated. The results are specified in Table 2. The bulk density of the obtained catalyst precursor molding was 0.64 g/ml, and the crushing strength (transverse direction), measured by Kiya type digital hardness tester, thereof was 9.1 kg.

TABLE 2

|  | Initial temp. of reaction [° C.] | Av. product compsn. [wt. %] | | | | Catalyst life [hr] |
| --- | --- | --- | --- | --- | --- | --- |
|  |  | C | 25X | 236T | 2346T |  |
| Example 2 | 472 | 3.0 | 19.9 | 65.1 | 1.7 | 513 |

(Note)
C: m-cresol,
25X: 2,5-xylenol,
236T: 2,3,6-trimethylphenol,
2346T: 2,3,4,6-tetramethylphenol.

The crushing strength (transverse direction), measured by Kiya type digital hardness tester, of the catalyst regenerated in the same manner as in Example 1 was 2.1 kg. The results are given in Table 5.

Example 3

Catalyst precursor molding of 3 mm diameter was prepared from 60 g of heavy basic magnesium carbonate, 140 g of light burned magnesia (trade name: Kyowamag 20, produced by Kyowa Chemical Industry Co., Ltd.) and 2.1 g of manganese oxalate in the same manner as in Example 1. The obtained catalyst precursor molding was charged into the reactor and activated in the same manner as in Example 1, and the catalytic performance thereof was evaluated.

The results are specified in Table 3. The bulk density of the obtained catalyst precursor molding was 0.72 g/ml, and the crushing strength (transverse direction), measured by Kiya type digital hardness tester, thereof was 9.9 kg.

TABLE 3

|  | Initial temp. of reaction [° C.] | Av. product compsn. [wt. %] | | | | Catalyst life [hr] |
| --- | --- | --- | --- | --- | --- | --- |
|  |  | C | 25X | 236T | 2346T |  |
| Example 3 | 472 | 3.1 | 20.0 | 64.7 | 1.9 | 408 |

(Note)
C: m-cresol,
25X: 2,5-xylenol,
236T: 2,3,6-trimethylphenol,
2346T: 2,3,4,6-tetramethylphenol.

The crushing strength (transverse direction), measured by Kiya type digital hardness tester, of the catalyst regenerated in the same manner as in Example 1 was 2.5 kg. The results are given in Table 5.

Comparative Example 1

Catalyst precursor molding of 3 mm diameter was prepared from 200 g of light burned magnesia (trade name: Kyowamag 20, produced by Kyowa Chemical Industry Co., Ltd.) and 0.15 g of manganese phosphate in the same manner as in Example 1. The obtained catalyst precursor molding was charged into the reactor and activated in the same manner as in Example 1, and the catalytic performance thereof was evaluated. The results are specified in Table 4. The bulk density of the obtained catalyst precursor molding was 1 g/ml, and the crushing strength (transverse direction), measured by Kiya type digital hardness tester, thereof was 9.3 kg.

TABLE 4

|  | Initial temp. of reaction [° C.] | Av. product compsn. [wt. %] | | | | Catalyst life [hr] |
| --- | --- | --- | --- | --- | --- | --- |
|  |  | C | 25X | 236T | 2346T |  |
| Comp. Ex. 1 | 479 | 2.2 | 20.6 | 64.8 | 1.9 | 308 |

(Note)
C: m-cresol,
25X: 2,5-xylenol,
236T: 2,3,6-trimethylphenol,
2346T: 2,3,4,6-tetramethylphenol.

The crushing strength (transverse direction), measured by Kiya type digital hardness tester, of the catalyst regenerated in the same manner as in Example 1 was 1.6 kg. The results are given in Table 5.

TABLE 5

|  | a/b (wt. ratio) | Catalyst | Concn. of 2,3,6-trimethylphenol 65% | | Crushing strength of catalyst (transverse direction) [kg] |
| --- | --- | --- | --- | --- | --- |
|  |  |  | initial temp. of reaction [° C.] | catalyst life [hr] |  |
| Example 1 | 7/3 | new | 468 | 596 | — |
|  |  | regenerated | 481 | 359 | 0.8 |
| Example 2 | 5/5 | new | 472 | 513 | — |
|  |  | regenerated | 482 | 383 | 2.1 |
| Example 3 | 3/7 | new | 472 | 408 | — |
|  |  | regenerated | 477 | 380 | 2.5 |
| Comp. Ex. 1 | 0/10 | new | 479 | 308 | — |
|  |  | regenerated | 485 | 273 | 1.6 |

(Note 1)
a: ground basic magnesium carbonate,
b: light burned magnesia.
(Note 2)
regenerated: first regenerated catalyst.
(Note 3)
crushing strength: orthomethylation reaction of m-cresol was performed in the presence of regenerated catalyst, catalyst was withdrawn, and the crushing strength thereof (3 mm diam.) was measured by Kiya type digital hardness tester.

What is claimed is:

1. An orthoalkylation catalyst for phenols, produced by calcining a catalyst precursor comprising basic magnesium carbonate (a) and magnesium oxide (b), wherein the basic magnesium carbonate (a) and the magnesium oxide (b) are mixed together at a weight ratio ((a)/(b)) of 20/80 to 80/20.

2. The orthoalkylation catalyst for phenols as claimed in claim 1, wherein the basic magnesium carbonate (a) is heavy magnesium carbonate.

3. The orthoalkylation catalyst for phenols as claimed in claim 1, wherein the magnesium oxide (b) is light burned magnesia.

4. The orthoalkylation catalyst for phenols as claimed in claim 2, wherein the magnesium oxide (b) is light burned magnesia.

5. The orthoalkylation catalyst for phenols as claimed in claim 1, wherein the catalyst precursor further comprises manganese oxalate (c) in an amount of 0.1 to 10% by weight based on the total (100% by weight) of basic magnesium carbonate (a) and magnesium oxide (b).

6. The orthoalkylation catalyst for phenols as claimed in claim 1, wherein the catalyst precursor is molded before calcination and the calcination is performed at 300 to 500° C. in the absence of molecular oxygen.

7. The orthoalkylation catalyst for phenols as claimed in claim 1, wherein the weight ratio ((a)/(b)) is 20/80 to 60/40.

8. The orthoalkylation catalyst for phenols as defined in any one of claims 1 to 7, wherein the orthoalkylation catalyst has a catalytic surface area of 25 to 500 m$^2$/g.

9. The orthoalkylation catalyst for phenols as defined in claim 1, wherein the catalyst precursor is formed by adding water to a mixture comprising magnesium carbonate (a) and magnesium oxide (b).

10. A process for producing an orthoalkylated phenol, which comprises performing a vapor phase reaction of a phenol with an alkyl alcohol in the presence of the orthoalkylation catalyst according to claim 1 so that an orthoalkylated phenol is obtained.

11. A process for producing an orthoalkylated phenol, which comprises performing a vapor phase reaction of a phenol with an alkyl alcohol in the presence of the orthoalkylation catalyst according to claim 9 so that an orthoalkylated phenol is obtained.

* * * * *